(12) United States Patent
Ljungqvist et al.

(10) Patent No.: US 6,602,977 B1
(45) Date of Patent: Aug. 5, 2003

(54) RECEPTOR STRUCTURES

(75) Inventors: Charlotta Ljungqvist, Bromma (SE); Karin Nord, Stockholm (SE); Per-Åke Nygren, Skarpnäck (SE); Mathias Uhlén, Täby (SE)

(73) Assignee: Biovitrum AB, Stockholm (SE)

( * ) Notice: Subject to any disclaimer, the term of this patent is extended or adjusted under 35 U.S.C. 154(b) by 0 days.

(21) Appl. No.: 09/549,441

(22) Filed: Apr. 14, 2000

Related U.S. Application Data

(60) Provisional application No. 60/131,004, filed on Apr. 23, 1999.

(30) Foreign Application Priority Data

Apr. 19, 1999 (SE) ................................................ 9901379

(51) Int. Cl.[7] ......................... A61K 38/00; C07K 16/00; C07K 5/00; C07K 1/00
(52) U.S. Cl. ......................... 530/300; 530/324; 530/350
(58) Field of Search .................. 530/300, 324, 530/350; 424/130.1, 141.1

(56) References Cited

U.S. PATENT DOCUMENTS

| 4,879,213 A | 11/1989 | Fox et al. |
| 4,954,618 A | 9/1990 | Fahnestock |
| 5,084,559 A | 1/1992 | Profy |
| 5,229,492 A | 7/1993 | Fahnestock |
| 5,312,901 A | 5/1994 | Fahnestock |
| 5,783,415 A | 7/1998 | Lee et al. |
| 5,831,012 A | * 11/1998 | Nilsson et al. |
| 6,013,763 A | * 1/2000 | Braisted et al. |
| 6,025,166 A | 2/2000 | Presta et al. |
| 6,027,927 A | 2/2000 | Presta et al. |

FOREIGN PATENT DOCUMENTS

WO   WO 9519374   7/1995

OTHER PUBLICATIONS

Nord et al, *Nature Biotechnology*, 15:772–777 (1997).
Nord et al, *Protein Engineering*, 8(6):601–608 (1995).
Cedergren et al., "Mutuational Analysis of the Interaction Between Staphylococcal Protein A and Human $IgG_1$," Protein Engineering 6(4):441–448 (1993).
Eliasson et al., "Chimeric IgG–Binding Receptors Engineered From Staphylococcal Protein A and Staphylococcal Protein G," The Journal of Biological Chemistry 263(9):4323–4327 (Mar. 25, 1988).

* cited by examiner

*Primary Examiner*—Mark Navarro
(74) *Attorney, Agent, or Firm*—Fish & Richardson P.C.

(57) ABSTRACT

The present invention relates to modified polypeptide derivatives of the B domain or Z domain of staphylococcal protein A (SPA). The derivatives contain amino acid substitutions that result in the ability of the B domain or Z domain to interact with at least one domain of a human Factor VIII protein, without substantially disrupting the structure and stability of the B domain or Z domain.

16 Claims, 7 Drawing Sheets

| | Sequence | |
|---|---|---|
| Zwt | VDNKFNKEQQNAFYEILHLPNLNEEQRNAFIQSLKDDPSQSANLLAEAKKLNDAQAPK | (SEQ ID NO: 1) |
| ZfVIII:1 | VDNKFNKEWRAAWVEIRGLPNLNWQQRKAFIVSLGDDPSQSANLLAEAKKLNDAQAPK | (SEQ ID NO: 2) |
| ZfVIII:2 | VDNKFNKEWRDAWVEIKYLPNLNVTQREAFIESLWDDPSQSANLLAEAKKLNDAQAPK | (SEQ ID NO: 3) |
| ZfVIII:3 | VDNKFNKEWRKAWVEIKVLPNLNESQKGAFIMSLLDDPSQSANLLAEAKKLNDAQAPK | (SEQ ID NO: 4) |
| ZfVIII:4 | VDNKFNKEWRLAWVEIRALPNLNPTQREAFILSLLDDPSQSANLLAEAKKLNDAQAPK | (SEQ ID NO: 5) |
| ZfVIII:5 | VDNKFNKEWREAWVEIGLLPNLNFTQGKAFIKSLLDDPSQSANLLAEAKKLNDAQAPK | (SEQ ID NO: 6) |
| ZfVIII:6 | VDNKFNKEVIVAVPEIAILPNLNPAQRAAFIASLRDDPSQSANLLAEAKKLNDAQAPK | (SEQ ID NO: 7) |
| ZfVIII mat.1 | VDNKFNKEWRNAWVEIKYLPNLNAAQRGAFISSLLDDPSQSANLLAEAKKLNDAQAPK | (SEQ ID NO: 8) |
| ZfVIII mat.2 | VDNKFNKEWRGAWVEIKGLPNLNYAQRQAFISSLLDDPSQSANLLAEAKKLNDAQAPK | (SEQ ID NO: 9) |
| ZfVIII mat.3 | VDNKFNKEWRMAWVEIKILPNLNWQRDAFIRSLLDDPSQSANLLAEAKKLNDAQAPK | (SEQ ID NO: 10) |
| ZfVIII mat.4 | VDNKFNKEWRRAWVEIKALPNLNWGQRNAFITSLLDDPSQSANLLAEAKKLNDAQAPK | (SEQ ID NO: 11) |
| ZfVIII mat.5 | VDNKFNKEWRRAAWVEIRNLPNLNWVQRSAFIDSLYDDPSLYDDPSQSANLLAEAKKLNDAQAPK | (SEQ ID NO: 12) |
| ZfVIII mat.6 | VDNKFNKEWRGAWVEIKTLPNLNEHWQRAAFIESLLDDPSQSANLLAEAKKLNDAQAPK | (SEQ ID NO: 13) |
| ZfVIII mat.7 | VDNKFNKEWRGAWVEIKTLPNLNYWQRDAFIASLVDDPSQSANLLAEAKKLNDAQAPK | (SEQ ID NO: 14) |
| ZfVIII mat.8 | VDNKFNKEWRVSWVEIKELPNLNWWQRRAFIQSLLDDPSQSANLLAEAKKLNDAQAPK | (SEQ ID NO: 15) |
| ZfVIII mat.9 | VDNKFNKEWREAWVEIKELPNLNWWQRRAFIQSLISSLLDDPSQSANLLAEAKKLNDAQAPK | (SEQ ID NO: 16) |
| ZfVIII mat.10 | VDNKFNKEWRLAWVEIKDLPNLNWRQRDAFISSLLDDPSQSANLLAEAKKLNDAQAPK | (SEQ ID NO: 17) |
| ZfVIII mat.11 | VDNKFNKEWRQAWVGIKKLPNLNWQRDAFIQSLFDDPSQSANLLAEAKKLNDAQAPK | (SEQ ID NO: 18) |
| ZfVIII mat.12 | VDNKFNKEWRAAWVEIKGLPNLNRPQRNAFIDSLYDDPSQSANLLAEAKKLNDAQAPK | (SEQ ID NO: 19) |
| ZfVIII mat.13 | VDNKFNKEWREAWVEIKNLPNLNWRQRDAFIVSLVDDPSQSANLLAEAKKLNDAQAPK | (SEQ ID NO: 20) |
| ZfVIII mat.14 | VDNKFNKEWRAAWVEIRELPNLNFIQRDAFIDSLLDDPSQSANLLAEAKKLNDAQAPK | (SEQ ID NO: 21) |
| ZfVIII mat.15 | VDNKFNKEWRSAWVEIKVLPNLNWQREAFIGSLLDDPSQSANLLAEAKKLNDAQAPK | (SEQ ID NO: 22) |

FIG. 1B

| | 10 20 30 40 50<br>123456789 123456789 123456789 123456789 123456789 12345678 | |
|---|---|---|
| $Z_{wt}$ | VDNKFNKEQQNAFYEILHLPNLNEEQRNAFIQSLKDDPSQSANLLAEAKKLNDAQAPK | (SEQ ID NO: 1) |
| $Z_{fVIII\ mat.16}$ | VDNKFNKEWRLAWVEIKGLPNLNWAQRQAFIDSLLDDPSQSANLLAEAKKLNDAQAPK | (SEQ ID NO: 23) |
| $Z_{fVIII\ mat.17}$ | VDNKFNKEWRTAWVEIKDLPNLNYYQRNAFIESLLDDPSQSANLLAEAKKLNDAQAPK | (SEQ ID NO: 24) |
| $Z_{fVIII\ mat.18}$ | VDNKFNKEWRTAWVEIKSLPNLNFGQRRAFIDSLLDDPSQSANLLAEAKKLNDAQAPK | (SEQ ID NO: 25) |
| $Z_{fVIII\ mat.19}$ | VDNKFNKEWREAWVEIKRLPNLNFEQRGAFIGSLLDDPSQSANLLAEAKKLNDAQAPK | (SEQ ID NO: 26) |
| $Z_{fVIII\ mat.20}$ | VDNKFNKEWRQAWVEIRGLPNLNWWQRDAFIESLLDDPSQSANLLAEAKKLNDAQAPK | (SEQ ID NO: 27) |
| $Z_{fVIII\ mat.21}$ | VDNKFNKEWRDAWVEIKSLPNLNWFQRDAFIASLLDDPSQSANLLAEAKKLNDAQAPK | (SEQ ID NO: 28) |
| $Z_{fVIII\ mat.22}$ | VDNKFNKEWREAWVEIKRLPNLNWYQRDAFIYSLLDDPSQSANLLAEAKKLNDAQAPK | (SEQ ID NO: 29) |
| $Z_{fVIII\ mat.23}$ | VDNKFNKEWRTAWVEIKLLPNLNWNQRAAFIDSLLDDPSQSANLLAEAKKLNDAQAPK | (SEQ ID NO: 30) |
| $Z_{fVIII\ mat.24}$ | VDNKFNKEWRLAWVEIKHLPNLNWWQRDAFIRSLLDDPSQSANLLAEAKKLNDAQAPK | (SEQ ID NO: 31) |
| $Z_{fVIII\ mat.25}$ | VDNKFNKEWREAWVEIKQLPNLNWWQREAFIGSLLDDPSQSANLLAEAKKLNDAQAPK | (SEQ ID NO: 32) |
| $Z_{fVIII\ mat.26}$ | VDNKFNKEWRMAWVEIKLLPNLNYFQRDAFIMSLLDDPSQSANLLAEAKKLNDAQAPK | (SEQ ID NO: 33) |
| $Z_{fVIII\ mat.27}$ | VDNKFNKEWRAAWVEIKRLPNLNWMQRDAFIVSLYDDPSQSANLLAEAKKLNDAQAPK | (SEQ ID NO: 34) |
| $Z_{fVIII\ mat.28}$ | VDNKFNKEWRDAWVEIKTLPNLNWYQRRAFIGSLLDDPSQSANLLAEAKKLNDAQAPK | (SEQ ID NO: 35) |
| $Z_{fVIII\ mat.29}$ | VDNKFNKEWREAWVEIKNLPNLNWRQRDAFIGSLLDDPSQSANLLAEAKKLNDAQAPK | (SEQ ID NO: 36) |
| $Z_{fVIII\ mat.30}$ | VDNKFNKEWRKAWVEIKTLPNLNWRQRDAFILSLYDDPSQSANLLAEAKKLNDAQAPK | (SEQ ID NO: 37) |
| $Z_{fVIII\ mat.31}$ | VDNKFNKEWRVAWVEIKNLPNLNWVQREAFIGSLLDDPSQSANLLAEAKKLNDAQAPK | (SEQ ID NO: 38) |
| $Z_{fVIII\ mat.32}$ | VDNKFNKEWRAAWVEIKRLPNLNWMQRDAFIVSLLDDPSQSANLLAEAKKLNDAQAPK | (SEQ ID NO: 39) |
| | VDNKFNKEWRKAWVEIKVLPNLNESQKGAFIMSLLDDPSQSANLLAEAKKLNDAQAPKC | (SEQ ID NO: 40) |

SEQUENCE LISTING

```
<160> NUMBER OF SEQ ID NOS: 40

<210> SEQ ID NO 1
<211> LENGTH: 58
<212> TYPE: PRT
<213> ORGANISM: Staphylococcus aureus

<400> SEQUENCE: 1

Val Asp Asn Lys Phe Asn Lys Glu Gln Gln Asn Ala Phe Tyr Glu Ile
  1               5                  10                  15

Leu His Leu Pro Asn Leu Asn Glu Glu Gln Arg Asn Ala Phe Ile Gln
             20                  25                  30

Ser Leu Lys Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 2
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 2

Val Asp Asn Lys Phe Asn Lys Glu Trp Arg Ala Ala Trp Val Glu Ile
  1               5                  10                  15

Arg Gly Leu Pro Asn Leu Asn Trp Gln Gln Arg Lys Ala Phe Ile Val
             20                  25                  30

Ser Leu Gly Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 3
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 3

Val Asp Asn Lys Phe Asn Lys Glu Trp Arg Asp Ala Trp Val Glu Ile
  1               5                  10                  15

Lys Tyr Leu Pro Asn Leu Asn Val Thr Gln Arg Glu Ala Phe Ile Glu
             20                  25                  30

Ser Leu Trp Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 4
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence
```

-continued

```
<400> SEQUENCE: 4

Val Asp Asn Lys Phe Asn Lys Glu Trp Arg Lys Ala Trp Val Glu Ile
 1               5                  10                  15

Lys Val Leu Pro Asn Leu Asn Glu Ser Gln Lys Gly Ala Phe Ile Met
             20                  25                  30

Ser Leu Leu Asp Asp Pro Ser Gln Ser Ala Asn Leu Leu Ala Glu Ala
         35                  40                  45

Lys Lys Leu Asn Asp Ala Gln Ala Pro Lys
         50                  55

<210> SEQ ID NO 5
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 5

Val Asp Asn Lys Phe Asn Lys Glu Trp Arg Leu Ala Trp Val Glu Ile
 1               5                  10                  15

Arg Ala Leu Pro Asn Leu Asn Pro Thr Gln Arg Glu Ala Phe Ile Leu
             20                  25                  30

Ser Leu Leu Asp Asp Pro Ser Gln Ser Ala Asn Leu Leu Ala Glu Ala
         35                  40                  45

Lys Lys Leu Asn Asp Ala Gln Ala Pro Lys
         50                  55

<210> SEQ ID NO 6
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 6

Val Asp Asn Lys Phe Asn Lys Glu Trp Arg Glu Ala Trp Val Glu Ile
 1               5                  10                  15

Gly Leu Leu Pro Asn Leu Asn Phe Thr Gln Gly Lys Ala Phe Ile Lys
             20                  25                  30

Ser Leu Leu Asp Asp Pro Ser Gln Ser Ala Asn Leu Leu Ala Glu Ala
         35                  40                  45

Lys Lys Leu Asn Asp Ala Gln Ala Pro Lys
         50                  55

<210> SEQ ID NO 7
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 7

Val Asp Asn Lys Phe Asn Lys Glu Val Ile Val Ala Val Pro Glu Ile
 1               5                  10                  15

Ala Ile Leu Pro Asn Leu Asn Pro Ala Gln Arg Ala Ala Phe Ile Ala
             20                  25                  30

Ser Leu Arg Asp Asp Pro Ser Gln Ser Ala Asn Leu Leu Ala Glu Ala
         35                  40                  45
```

Lys Lys Leu Asn Asp Ala Gln Ala Pro Lys
    50                  55

<210> SEQ ID NO 8
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 8

Val Asp Asn Lys Phe Asn Lys Glu Trp Arg Asn Ala Trp Val Glu Ile
 1               5                  10                  15

Lys Tyr Leu Pro Asn Leu Asn Ala Ala Gln Arg Gly Ala Phe Ile Ser
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 9
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 9

Val Asp Asn Lys Phe Asn Lys Glu Trp Arg Gly Ala Trp Val Glu Ile
 1               5                  10                  15

Lys Gly Leu Pro Asn Leu Asn Tyr Ala Gln Arg Gln Ala Phe Ile Ser
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 10
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 10

Val Asp Asn Lys Phe Asn Lys Glu Trp Arg Met Ala Trp Val Glu Ile
 1               5                  10                  15

Lys Ile Leu Pro Asn Leu Asn Trp Trp Gln Arg Asp Ala Phe Ile Arg
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 11
<211> LENGTH: 58
<212> TYPE: PRT
<213> ORGANISM: Artificial Sequence
<220> FEATURE:

```
<223> OTHER INFORMATION: Description of Artificial Sequence: Modified
      bacterial receptor sequence

<400> SEQUENCE: 11

Val Asp Asn Lys Phe Asn Lys Glu Trp Arg Arg Ala Trp Val Glu Ile
 1               5                  10                  15

Lys Ala Leu Pro Asn Leu Asn Trp Gly Gln Arg Asn Ala Phe Ile Thr
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 12
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 12

Val Asp Asn Lys Phe Asn Lys Glu Trp Arg Arg Ala Trp Val Glu Ile
 1               5                  10                  15

Arg Asn Leu Pro Asn Leu Asn Trp Val Gln Arg Ser Ala Phe Ile Asp
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 13
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 13

Val Asp Asn Lys Phe Asn Lys Glu Trp Arg Gly Ala Trp Val Glu Ile
 1               5                  10                  15

Lys Thr Leu Pro Asn Leu Asn His Trp Gln Arg Ala Ala Phe Ile Glu
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 14
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 14

Val Asp Asn Lys Phe Asn Lys Glu Trp Arg Gly Ala Trp Val Glu Ile
 1               5                  10                  15

Lys Thr Leu Pro Asn Leu Asn Tyr Trp Gln Arg Asp Ala Phe Ile Ala
            20                  25                  30
```

Ser Leu Val Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 15
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 15

Val Asp Asn Lys Phe Asn Lys Glu Trp Arg Val Ser Trp Val Glu Ile
 1               5                  10                  15

Lys Glu Leu Pro Asn Leu Asn Trp Trp Gln Arg Arg Ala Phe Ile Gln
                20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 16
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 16

Val Asp Asn Lys Phe Asn Lys Glu Trp Arg Glu Ala Trp Val Glu Ile
 1               5                  10                  15

Lys Glu Leu Pro Asn Leu Asn Trp Trp Gln Arg Arg Ala Phe Ile Gln
                20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 17
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 17

Val Asp Asn Lys Phe Asn Lys Glu Trp Arg Leu Ala Trp Val Glu Ile
 1               5                  10                  15

Lys Asp Leu Pro Asn Leu Asn Trp Arg Gln Arg Asp Ala Phe Ile Ser
                20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 18
<211> LENGTH: 58

```
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 18

Val Asp Asn Lys Phe Asn Lys Glu Trp Arg Gln Ala Trp Val Gly Ile
 1               5                  10                  15

Lys Lys Leu Pro Asn Leu Asn Tyr Trp Gln Arg Asp Ala Phe Ile Gln
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 19
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 19

Val Asp Asn Lys Phe Asn Lys Glu Trp Arg Ala Ala Trp Val Glu Ile
 1               5                  10                  15

Lys Gly Leu Pro Asn Leu Asn Arg Pro Gln Arg Asn Ala Phe Ile Asp
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 20
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 20

Val Asp Asn Lys Phe Asn Lys Glu Trp Arg Glu Ala Trp Val Glu Ile
 1               5                  10                  15

Lys Asn Leu Pro Asn Leu Asn Trp Arg Gln Arg Asp Ala Phe Ile Val
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 21
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 21

Val Asp Asn Lys Phe Asn Lys Glu Trp Arg Ala Ala Trp Val Glu Ile
 1               5                  10                  15
```

```
Arg Glu Leu Pro Asn Leu Asn Phe Ile Gln Arg Asp Ala Phe Ile Asp
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 22
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 22

Val Asp Asn Lys Phe Asn Lys Glu Trp Arg Ser Ala Trp Val Glu Ile
 1               5                  10                  15

Lys Val Leu Pro Asn Leu Asn Trp Trp Gln Arg Glu Ala Phe Ile Gly
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 23
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 23

Val Asp Asn Lys Phe Asn Lys Glu Trp Arg Leu Ala Trp Val Glu Ile
 1               5                  10                  15

Lys Gly Leu Pro Asn Leu Asn Trp Ala Gln Arg Gln Ala Phe Ile Asp
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 24
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 24

Val Asp Asn Lys Phe Asn Lys Glu Trp Arg Thr Ala Trp Val Glu Ile
 1               5                  10                  15

Lys Asp Leu Pro Asn Leu Asn Tyr Tyr Gln Arg Asn Ala Phe Ile Glu
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 25
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 25

Val Asp Asn Lys Phe Asn Lys Glu Trp Arg Thr Ala Trp Val Glu Ile
 1               5                  10                  15

Lys Ser Leu Pro Asn Leu Asn Phe Gly Gln Arg Arg Ala Phe Ile Asp
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 26
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 26

Val Asp Asn Lys Phe Asn Lys Glu Trp Arg Glu Ala Trp Val Glu Ile
 1               5                  10                  15

Lys Arg Leu Pro Asn Leu Asn Phe Gln Gln Arg Gly Ala Phe Ile Gly
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 27
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 27

Val Asp Asn Lys Phe Asn Lys Glu Trp Arg Gln Ala Trp Val Glu Ile
 1               5                  10                  15

Arg Gly Leu Pro Asn Leu Asn Trp Trp Gln Arg Asp Ala Phe Ile Glu
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 28
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 28

```
Val Asp Asn Lys Phe Asn Lys Glu Trp Arg Asp Ala Trp Val Glu Ile
 1               5                  10                  15

Lys Ser Leu Pro Asn Leu Asn Trp Phe Gln Arg Asp Ala Phe Ile Ala
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 29
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 29

Val Asp Asn Lys Phe Asn Lys Glu Trp Arg Glu Ala Trp Val Glu Ile
 1               5                  10                  15

Lys Arg Leu Pro Asn Leu Asn Trp Tyr Gln Arg Asp Ala Phe Ile Tyr
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 30
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 30

Val Asp Asn Lys Phe Asn Lys Glu Trp Arg Thr Ala Trp Val Glu Ile
 1               5                  10                  15

Lys Leu Leu Pro Asn Leu Asn Trp Asn Gln Arg Ala Ala Phe Ile Asp
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 31
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 31

Val Asp Asn Lys Phe Asn Lys Glu Trp Arg Leu Ala Trp Val Glu Ile
 1               5                  10                  15

Lys His Leu Pro Asn Leu Asn Trp Trp Gln Arg Asp Ala Phe Ile Arg
            20                  25                  30

Ser Leu Leu Asp Asp Pro Ser Gln Ser Ala Asn Leu Leu Ala Glu Ala
        35                  40                  45
```

Lys Lys Leu Asn Asp Ala Gln Ala Pro Lys
    50                  55

<210> SEQ ID NO 32
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 32

Val Asp Asn Lys Phe Asn Lys Glu Trp Arg Glu Ala Trp Val Glu Ile
 1               5                  10                  15

Lys Gln Leu Pro Asn Leu Asn Trp Trp Gln Arg Glu Ala Phe Ile Gly
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 33
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 33

Val Asp Asn Lys Phe Asn Lys Glu Trp Arg Met Ala Trp Val Glu Ile
 1               5                  10                  15

Lys Leu Leu Pro Asn Leu Asn Tyr Phe Gln Arg Asp Ala Phe Ile Met
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 34
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 34

Val Asp Asn Lys Phe Asn Lys Glu Trp Arg Ala Ala Trp Val Glu Ile
 1               5                  10                  15

Lys Arg Leu Pro Asn Leu Asn Trp Met Gln Arg Asp Ala Phe Ile Val
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 35
<211> LENGTH: 58
<212> TYPE: PRT
<213> ORGANISM: Artificial Sequence
<220> FEATURE:
<223> OTHER INFORMATION: Description of Artificial Sequence: Modified bacterial receptor sequence

<400> SEQUENCE: 35

Val Asp Asn Lys Phe Asn Lys Glu Trp Arg Asp Ala Trp Val Glu Ile
1               5                   10                  15

Lys Thr Leu Pro Asn Leu Asn Trp Tyr Gln Arg Arg Ala Phe Ile Gly
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 36
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 36

Val Asp Asn Lys Phe Asn Lys Glu Trp Arg Glu Ala Trp Val Glu Ile
1               5                   10                  15

Lys Asn Leu Pro Asn Leu Asn Trp Arg Gln Arg Asp Ala Phe Ile Gly
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 37
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 37

Val Asp Asn Lys Phe Asn Lys Glu Trp Arg Lys Ala Trp Val Glu Ile
1               5                   10                  15

Lys Thr Leu Pro Asn Leu Asn Trp Arg Gln Arg Asp Ala Phe Ile Leu
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 38
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 38

Val Asp Asn Lys Phe Asn Lys Glu Trp Arg Val Ala Trp Val Glu Ile
1               5                   10                  15

Lys Asn Leu Pro Asn Leu Asn Trp Val Gln Arg Glu Ala Phe Ile Gly
            20                  25                  30

-continued

```
Ser Leu Leu Asp Asp Pro Ser Gln Ser Ala Asn Leu Leu Ala Glu Ala
            35                  40                  45

Lys Lys Leu Asn Asp Ala Gln Ala Pro Lys
     50                  55

<210> SEQ ID NO 39
<211> LENGTH: 58
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 39

Val Asp Asn Lys Phe Asn Lys Glu Trp Arg Ala Ala Trp Val Glu Ile
 1               5                  10                  15

Lys Arg Leu Pro Asn Leu Asn Trp Met Gln Arg Asp Ala Phe Ile Val
            20                  25                  30

Ser Leu Leu Asp Asp Pro Ser Gln Ser Ala Asn Leu Leu Ala Glu Ala
            35                  40                  45

Lys Lys Leu Asn Asp Ala Gln Ala Pro Lys
     50                  55

<210> SEQ ID NO 40
<211> LENGTH: 59
<212> TYPE: PRT
<213> ORGANISM: Artificial Sequence
<220> FEATURE:
<223> OTHER INFORMATION: Description of Artificial Sequence: Modified
      bacterial receptor sequence

<400> SEQUENCE: 40

Val Asp Asn Lys Phe Asn Lys Glu Trp Arg Lys Ala Trp Val Glu Ile
 1               5                  10                  15

Lys Val Leu Pro Asn Leu Asn Glu Ser Gln Lys Gly Ala Phe Ile Met
            20                  25                  30

Ser Leu Leu Asp Asp Pro Ser Gln Ser Ala Asn Leu Leu Ala Glu Ala
            35                  40                  45

Lys Lys Leu Asn Asp Ala Gln Ala Pro Lys Cys
     50                  55
```

RECEPTOR STRUCTURES

CROSS REFERENCE TO RELATED APPLICATIONS

This application claims priority from Swedish Patent Application No. 9901379-9, filed Apr. 19, 1999, and U.S. Provisional Patent Application Ser. No. 60/131,004, filed Apr. 23, 1999.

TECHNICAL FIELD

The present invention relates to polypeptides which are derivatives of a staphylococcal protein A (SPA) domain, more specifically the B or Z domain, wherein between 1 and 20 amino acid residues of the said SPA domain have been substituted by other amino acid residues, said substitution resulting in interaction capacity of the said polypeptide with human Factor VIII protein. The said polypeptides are useful e.g. in the purification of Factor VIII protein and in diagnosis of hemophilia.

BACKGROUND ART

Modified Bacterial Receptor Structures

Random mutagenesis in combination with an efficient phenotypic selection procedure has proved to be an important tool in molecular biology to analyze the structure and function of proteins. Interesting targets for random mutagenesis followed by phenotypic selection are solvent-exposed surfaces of bacterial receptors. Such proteins can be unusually stable, which makes them suitable for various applications (Alexander et al. (1992) Biochemistry 31, 3597–3603). In particular, for bacterial receptors containing helix bundle structures, the conformation can be expected to be tolerant to changes in the side chains of residues not involved in helix packing interfaces. Examples of such molecules are the relatively small (58 residues) IgG-binding domain B of staphylococcal protein A (SPA) and the synthetic analogue of domain B, designated domain Z (Nilsson et al. (1987) Protein Engineering 1, 107–113).

The SPA-derived domain Z (SEQ ID NO: 1) has been utilized as a scaffold for constructing domain variants with new functions. Repertoires of mutant Z domain genes were assembled and inserted into a phagemid vector adapted for monovalent phage display of Z domain variants. Two combinatorial libraries, each comprising approximately $4 \times 10^7$ transformants, were constructed. Selection against different target proteins, viz. Taq DNA polymerase, human insulin and a human apolipoprotein A-1 variant, was performed. The obtained binding proteins were referred to as "affibodies". See WO 95/19374; Nord et al. (1995) Protein Engineering, Vol. 8 (6), 601–608 (hereinafter referred to as Nord-95); and Nord et al. (1997) Nature Biotechnology, Vol. 15, 772–777 (hereinafter referred to as Nord-97).

Hemophilia and Factor VIII Deficiency

Hemophilia is an inherited disease which has been known for centuries, but it is only within the last four decades that it has been possible to differentiate between the various forms; hemophilia A and hemophilia B. Hemophilia A is the most frequent form. It affects only males with an incidence of one or two individuals per 10,000 liveborn males. The disease is caused by a strongly decreased level or absence of biologically active coagulation Factor VIII (also known as antihemophilic factor, AHF), which is a protein normally present in plasma.

Therapeutic Factor VIII concentrates for the treatment of hemophilia have been prepared by fractionation of plasma. Factor VIII concentrates derived from human plasma contain several fragmented fully active Factor VIII forms as described by Andersson et al. (1986) Proc. Natl. Acad. Sci. USA 83, 2979–2983. The smallest active form hitherto described has a molecular mass of 170 kDa and consists of two chains of 90 kDa and 80 kDa, respectively, held together by metal ion(s). Reference is here made to EP-A-0 197 901.

However, methods are also available for production of Factor VIII in cell culture using recombinant DNA techniques, as reported e.g. by Wood et al. (1984) Nature 312, 330–337 and in EP-A-0 160 457. The structure and biochemistry of recombinant Factor VIII products in general have been described by Kaufman, R. J. in Trends in Biotechnology Vol. 9(10), 353–359, 1991; and in Hematology Vol. 63, 155–165, 1991. A recombinant Factor VIII form, termed r-VIII SQ, which corresponds to the 170 kDa plasma form, is described in WO 91/09122.

There is a need for new polypeptides which have interaction capacity with the Factor VIII protein and which can be used e.g. for purification of Factor VIII, for diagnosis of conditions related to Factor VIII deficiency, such as hemophilia, in therapy, or for research purposes.

BRIEF DESCRIPTION OF THE DRAWINGS

FIG. 1

Amino acid sequences (one-letter code) of the Z domain derived from Staphylococcus aureus protein A ($Z_{wt}$) and modified polypeptides (affibodies) according to the invention. The 13 positions chosen for random mutagenesis during construction of the combinatorial libraries are indicated with boldface letters.

FIG. 2

Sensorgrams from Biospecific Interaction Analysis of the affibody $Z_{fVIII:3}$ (SEQ ID NO: 4) with Factor rVIII (panel A); the 80 kDa chain of Factor rVIII (panel B); and polyclonal human IgG (panel C).

FIG. 3

Overlay plot of sensorgrams from a competitive binding assay with affibody $Z_{fVIII:3}$ (SEQ ID NO: 4) using the monoclonal antibody 8A4 as a competitor and polyclonal human IgG as a negative control competitor. Three different samples (Pure rVIII; rVIII mixed with mAb 8A4; and rVIII mixed with polyclonal IgG) were injected over the affibody surface.

Figure 4A:
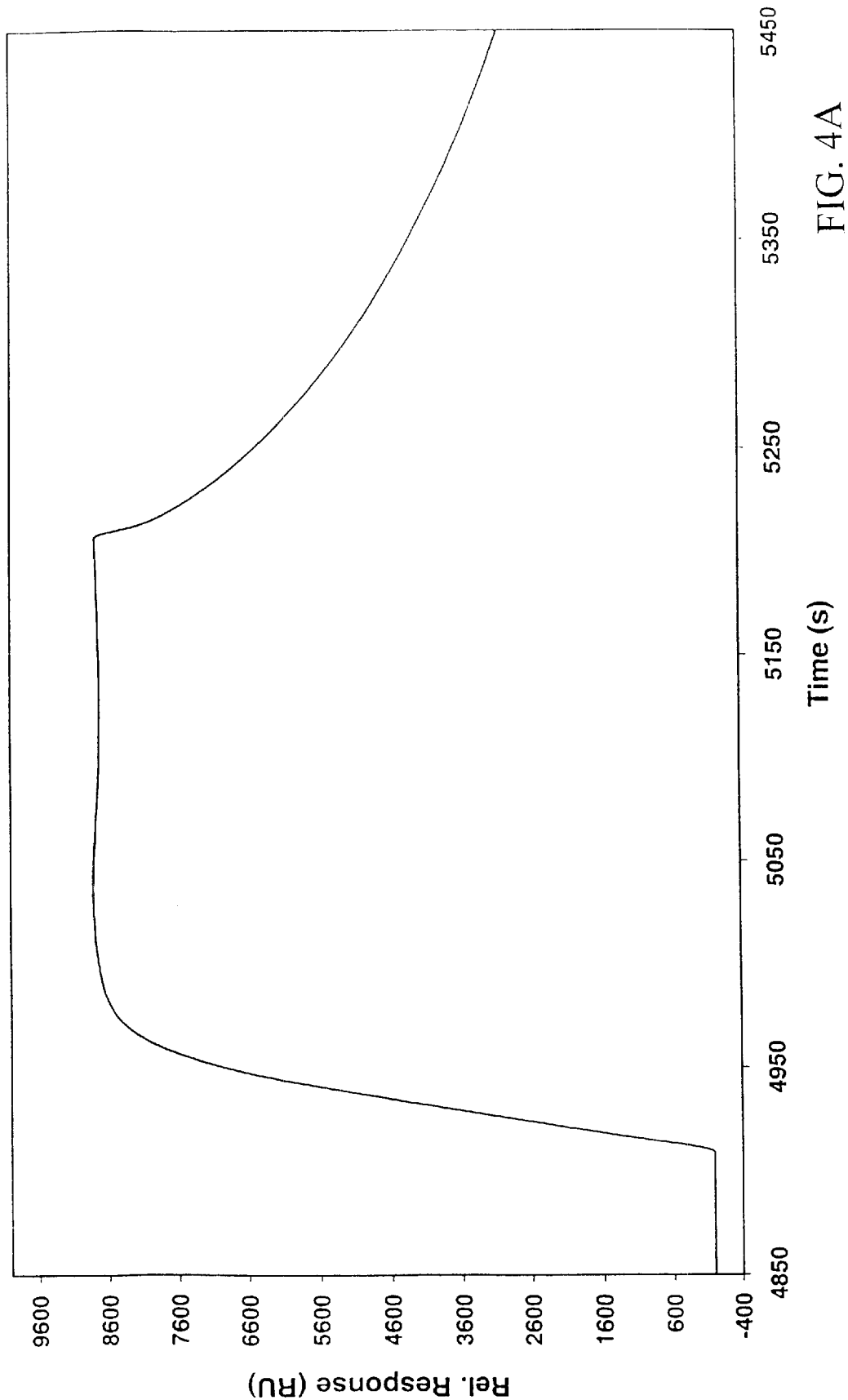
Figure 4B:
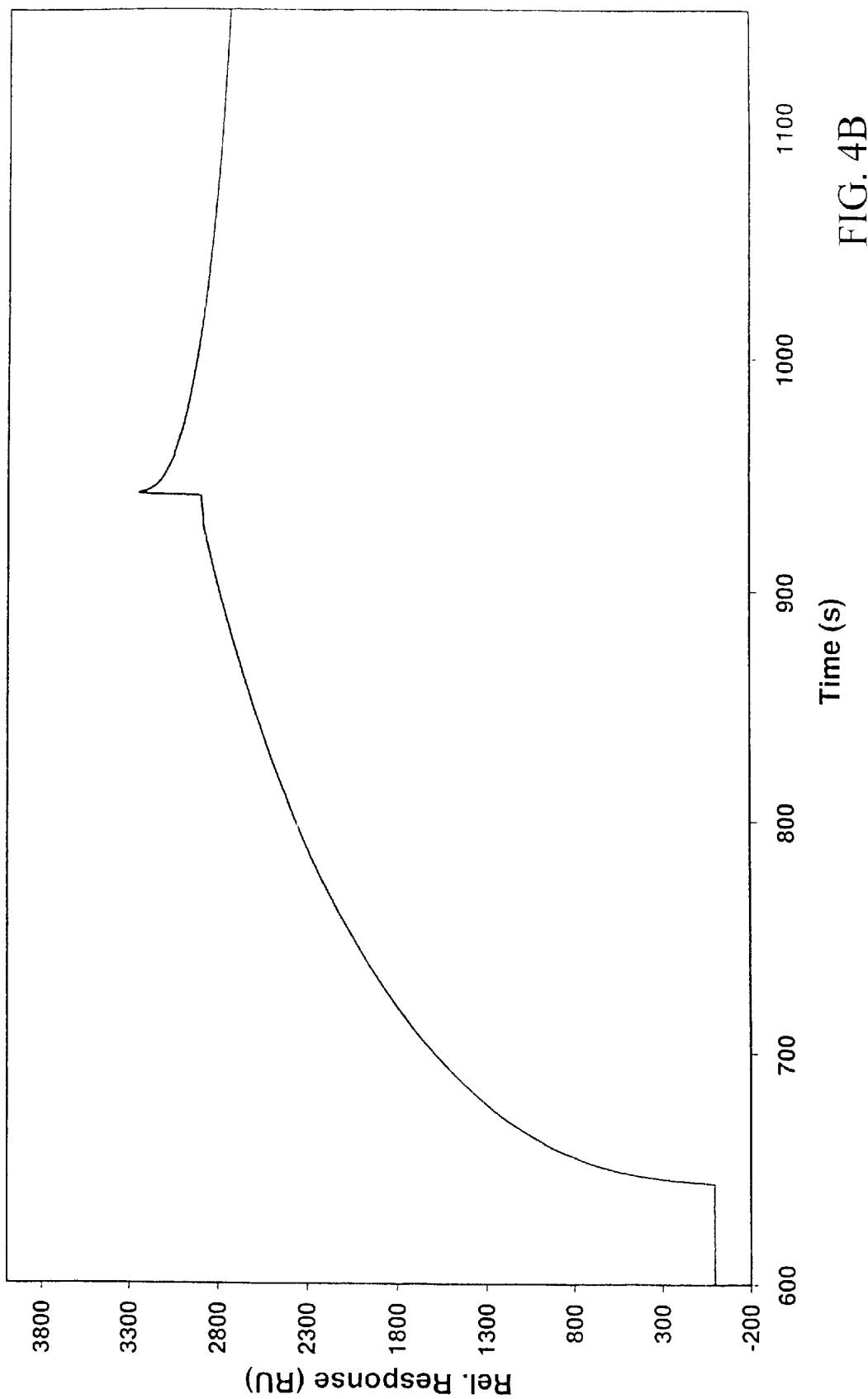

FIGS. 4A and 4B

Sensorgrams from binding analysis of Factor VIII injected over a synthetic affibody (SEQ ID NO: 40) surface:

(A) Affibody binding to recombinant Factor VIII (rVIII);

(B) Affibody binding to blood plasma containing Factor VIII.

FIG. 5

Overlay plot of sensorgrams from binding analysis of recombinant Factor VIII (rVIII) with equimolar concentrations of second generation affibodies $Z_{fVIII\ mat:26}$ (SEQ ID NO: 33); $Z_{fVIII\ mat:28}$ (SEQ ID NO: 35) and $Z_{fVIII\ mat:31}$ (SEQ ID NO: 38), as well as the first generation affibody $Z_{fVIII:3}$ (SEQ ID NO: 4).

DISCLOSURE OF THE INVENTION

The present invention provides modified polypeptides (affibodies) which have interaction capacity with Factor VIII protein and which can be used e.g. in methods for analysis of Factor VIII and purification of Factor VIII. The said affibodies could also be used e.g. as lead compounds for the identification of small molecules interacting with Factor VIII, said small molecules being potentially useful in therapy.

The polypeptides ("affibodies") according to the invention have several advantages over traditional antibodies, e.g. (i) a lower cost of manufacture; (ii) smaller size; (iii) increased stability and robustness; and (iv) the ability of being produced recombinantly in a bacterial host, or by chemical synthesis, which obviates the risk for viral contamination.

Consequently, in a first aspect, the present invention provides a polypeptide which is a derivative of a staphylococcal protein A (SPA) domain, said SPA domain being the B or Z domain, wherein a number of the amino acid residues have been substituted by other amino acid residues, said substitution being made without substantial loss of the basic structure and stability of the said SPA domain, and said substitution resulting in interaction capacity of the said polypeptide with at least one domain of human Factor VIII protein. The number of substituted amino acid residues could be from 1 to about 20, or from 1 to about 13. Other possible ranges are from 4 to about 20; from 4 to about 13; from 5 to about 20, or from 5 to about 13 amino acid residues. It will be understood by the skilled person, e.g. from the references Nord-95 and Nord-97, that preferentially amino residues located on the surface of the Z-domain can be substituted, while the core of the bundle should be kept constant to conserve the structural properties of the molecule.

In the present context the term "derivative" includes polypeptides having additional amino acid residues at the N- or C-terminal end. Additional amino acid residues could be included for various reasons concerning production, purification or stabilization, such as e.g. for facilitated coupling to chromatographic resins. The invention thus includes polypeptides (affibodies) which are longer than the SPA domain from which they are derived, but which still have interaction capacity with Factor VIII.

The said SPA domain Z has preferably the amino acid sequence set forth as SEQ ID NO: 1. However, the term "domain Z" also includes variants of domain Z having essentially the same basic structure and stability as the SPA domain Z.

Preferably, at least 4 amino acid residues of the said SPA domain have been substituted by other amino acid residues. The substituted amino acid residues can e.g. be those in positions 9, 10, 13 and 14, or positions 9, 10, 13, 14 and 17, in SEQ ID NO: 1. In addition, one or more of the amino acid residues in positions 11, 18, 24, 25, 27, 28, 32 and 35 in SEQ ID NO: 1 can be substituted by other amino acid residues. As indicated above, it will be understood that other amino acid residues can be substituted provided that the basic structural properties of the domain Z are maintained.

In a particularly preferred form, the invention includes polypeptides wherein the amino acid residue in position 9 in SEQ ID NO: 1 has been substituted by a tryptophane (W) residue; position 10 by an arginine (R) residue, position 13 by a tryptophane (W) residue and position 14 by a valine (V) residue.

The invention also includes polypeptides wherein the amino acid residue in position 17 in SEQ ID NO: 1 has been substituted by an arginine (R), glycine (G), alanine (A) or, preferably, a lysine (K) residue; as well as polypeptides wherein the amino acid residue in position 35 in SEQ ID NO: 1 has been substituted by a glycine (G), tryptophane (W), arginine (R), tyrosine (Y), valine (V), phenylalanine (F) or, preferably, leucine (L) residue.

The term "domain of human Factor VIII protein" includes in particular the 90 kDa and 80 kDa domains. Polypeptides according to the invention, wherein the Factor VIII domain is the 90 kDa domain, could e.g. have the amino acid sequence set forth in any one of SEQ ID NOS: 2 to 6, or 8 to 39. A polypeptide according to the invention, wherein the Factor VIII domain is the 80 kDa domain, could e.g. have the amino acid sequence set forth in SEQ ID NO: 7.

In a further aspect, the invention provides a process for the manufacture of a polypeptide (affibody) as defined above, said process comprising the steps (i) displaying, by e.g. phage display (for a review, see e.g. Kay, K. et al. (eds.) Phage Display of Peptides and Proteins: A Laboratory Manual, Academic Press, San Diego, ISBN 0-12-402380-0), ribosomal display (for a review, see e.g. Hanes, J. et al. (1998) Proc. Natl. Acad. Sci. USA 95(24), 14130–14135) or cell display (for a review, see e.g. Daugherty, P.S. et al. (1998) Protein Eng. 11(9), 825–832), polypeptide variants from a protein library embodying a repertoire of polypeptide variants derived from SPA domain B or Z;

(ii) selecting clones expressing polypeptides that bind to human Factor VIII protein; and (iii) producing polypeptides by recombinant expression of the selected clones or by chemical synthesis.

The said SPA domain is preferably the Z domain having, as discussed above, essentially the amino acid sequence set forth as SEQ ID NO: 1. The various steps of the process can be performed by the skilled person by methods disclosed in the present description, in particular in the following examples, and by methods known in the art.

In yet another aspect, the invention provides a method for purification of human Factor VIII protein, comprising interaction of a polypeptide (affibody), as defined above, with the said human Factor VIII protein. Such a method could e.g. comprise the steps (a) coupling a polypeptide (affibody) according to the invention to a matrix, said matrix being prepared from e.g. sepharose, silica, cellulose or membranes.

(b) contacting a sample containing human Factor VIII protein to the matrix, so that said human Factor VIII protein interacts with the said polypeptide;

(c) washing the matrix under conditions, such as the conditions described in Example 6, below, suitable for maintaining the interaction between human Factor VIII protein and the affibody; and (d) recovering biologically active human Factor VIII protein, by e.g. elution with ethylene glycol.

The said human Factor VIII protein can be derived from human plasma or produced by recombinant DNA techniques well known in the art. The term "Factor VIII protein" is intended to include derivatives having essentially the biological functions of wild-type Factor VIII. Such a Factor VIII derivative could e.g. be a deletion derivative lacking one or more amino acids in the region between amino acids 740 and 1649 (the B domain), as disclosed in WO 91/09122. Other Factor VIII derivatives are disclosed in WO 92/16557. It will be understood that the part of the Factor VIII protein interacting with the affibody could be the 90 kDa or the 80 kDa domain, depending on the specificity of the used affibody.

EXAMPLES

Example 1

Construction of Libraries

The previously described libraries Z-lib1 and Z-lib2 (Nord-95 and Nord-97), based on the synthetic 58-residue SPA domain Z (Nilsson et al. (1987) Protein Engineering 1, 107–113), were used for selection of novel binding proteins directed against recombinant Factor VIII (hereinafter also referred to as rVIII). In the construction of the Z domain libraries, 13 surface located residues (Q9, Q10, N11, F13, Y14, L17, H18, E24, E25, R27, N28, Q32 and K35) in helices 1 and 2 of the three helix bundle Z domain were targeted for randomization using a NN(G/T) codon degeneracy in Z-lib1 and a (C/A/G)NN degeneracy in Z-lib2. The libraries were adopted for monovalent display on filamentous bacteriophage surfaces through fusion to a truncated version of phage coat protein 3.

Phage stocks for biopanning rounds were prepared using standard procedures involving helper phage M13K07 (New England Biolabs, Beverly, Mass.) routinely yielding titers in the range of $10^{11}$ to $10^{12}$ colony forming units per ml, after polyethylene glycol precipitation.

Example 2

Selection of First Generation Affibodies (a) Biotinylation and Immobilization of Recombinant Factor VIII The target protein, recombinant Factor VIII with the B-domain deleted (hereinafter referred to as rVIII) was obtained essentially as described in WO 91/09122 and in vitro biotinylated in order to enable a robust immobilization onto streptavidin coated paramagnetic beads for the biopanning procedure, using a biotinylation kit (EZ-Link™; Sulfo-NHS-LC-Biotin, prod no. 21335, Pierce Chemical Company, Rockford, Ill.). Approximately 100 $\mu$g of the in vitro biotinylated rVIII was mixed with 5 mg of pre-washed (according to the suppliers recommendations) streptavidin coated paramagnetic beads (SA beads) (Dynabeads M-280 Streptavidin, Dynal AS, Oslo, Norway) in a final volume of 1 ml binding buffer (0.1 M ammonium acetate, 5 mM calcium chloride, 0.8 M sodium chloride, 0.02% Tween-20, pH 6.1), and incubated on a rotator for 1 hour at room temperature and 2 hours at +4° C. The SA beads with the immobilized rVIII were subsequently washed six times with binding buffer. This procedure resulted in the immobilization of approximately 10 $\mu$g of the 90 kDa chain of rVIII per 5 mg of SA beads, as determined by SDS-PAGE analysis.

(b) Biopanning

Four rounds of biopanning (affinity-based selection), in the presence of a five-fold molar excess of the 80 kDa chain of rVIII in solution (in order to eliminate most of the potential 80 kDa chain binders), with increasing amounts of washing in each cycle were performed. Elutions with low pH and ethylene glycol were performed in parallel biopannings.

Biopanning was performed as follows: In the first cycle, 100 $\mu$l phage stock from either Z-lib1 or Z-lib2, 90 $\mu$l of the 80 kDa chain of rVIII in solution (approximately 2.5 $\mu$M) and 10 $\mu$l 2% gelatin solution were added to two tubes of dry SA beads with immobilized rVIII and incubated on a rotator at room temperature for two hours. The SA beads were washed once with binding buffer (5 minutes washing time) and bound phage particles were subsequently eluted with 0.5 ml glycine-HCl, pH 2.2 for 10 minutes at room temperature. The supernatants were immediately neutralized with 50 $\mu$l of 1 M Tris-Cl, pH 8.5. Eluted phage particles were used to infect 1 ml of log phase ($A_{600}\approx 1$) E. coli RR1$\Delta$M15 cells (Ruither (1982) Nucleic Acid Research 10, 5765–5772) for 20 min at +37° C. and were thereafter spread onto TYE (per liter: 15 g agar, 8 g BaCl, 10 g Tryptone and 5 g yeast extract) agar plates supplemented with glucose 2% and ampicillin (100 mg/l), for the preparation of new phage stocks.

In the second cycle, two tubes of SA beads containing biotinylated rVIII were incubated with 50 $\mu$l phage stock from the biopanning with Z-lib1 mixed with 50 $\mu$l phage stock from the biopanning with Z-lib2 in the first cycle. Otherwise, conditions were the same as in the first cycle. The SA beads were washed three times with binding buffer and twice with washing buffer (50 mM calcium chloride, 50 mM histidine, 0.05% Tween-20, pH 6.6) (25 min. total washing time). One of the tubes was eluted with glycine-HCl, pH 2.2, as before, but for 20 min., and the other tube was eluted with elution buffer (50 mM calcium chloride, 50 mM histidine, 0.02% Tween-20, 50% ethylene glycol, pH 6.6) for 20 min. at room temperature.

In the third cycle, the conditions were the same as in cycle two, except that the phage stock input in one tube was prepared from the eluted phage from the pH 2.2 elution in the previous cycle, and the input in the other tube was prepared from the ethylene is glycol elution. The SA beads were washed five times with binding buffer and five times with washing buffer (approximately 1 hour total washing time). The elution was done as before with pH 2.2 elution in the tube with the pH 2.2 eluted input phage stock and ethylene glycol elution in the tube with the ethylene glycol eluted input phage stock. Cycle four was performed exactly as cycle three.

The eluted phages from each panning round were titrated by infecting log phase RR1$\Delta$M15 cells (OD at 600 nm$\approx$0.5) with serial dilutions of the eluate at +37° C. for 20 min. The rest of the eluted phages were used to infect 10 ml of the cells. The cells were spread on TYE agar plates supplemented with 2% glucose and 100 $\mu$g/ml ampicillin and the plates were incubated at +37° C. over night. The colonies were collected and used to inoculate TSB supplemented with 1 % glucose and 100 $\mu$g/ml ampicillin, for preparation of a new phage stock for the next round of panning. After the last panning round, reinfected cells were spread on plates to yield clones for DNA sequence analysis of selected Z domain variants.

(c) DNA Sequencing

Solid phase sequencing (Hultman et al. (1989) Nucleic Acid Research 17, 4937–4946) of twenty of the selected affibody clones from the fourth cycle (ten from the elution with pH 2.2 and ten from the elution with ethylene glycol) was performed by employing the indodicarbocyanine dye ALFred (Cy5) phosphoramidite labeled sequencing primer NOKA-3 on a robotic workstation (Biomek 1000, Beckman Instruments, Fullerton, Calif.). The Sanger-fragments were analyzed on an ALFexpress™ (Amersham Pharmacia Biotech, Uppsala, Sweden). Nine different sequences were identified, some represented by more than one clone.

Example 3

Production and Purification of First Generation Affibodies

Nine different affibodies, identified in the DNA sequencing step, were produced as soluble secreted proteins, fused to a 5 kDa serum albumin binding domain (ABD) from staphylococcal protein G (SPG) (Nilsson et al. (1994) Eur. J. Biochem. 224, 103–108), as encoded from the phagemid vector (Nord-97), in a non-suppressor strain, E. coli RV308 (Maurer et al. (1980) J. Mol. Biol. 139, 147–161). The affibody-ABD fusion proteins were released from the periplasm and purified by affinity chromatography on an HSA-Sepharose column (Nygren et al. (1988) J. Mol. Recogn. 1, 69–74) and expression levels in this expression system were in the range of 10 mg/l shake flask culture.

Example 4

Biospecific Interaction Analysis of First Generation Affibodies

A BIAcore® 2000 instrument (Biacore AB, Uppsala, Sweden) was employed for real-time Biospecific Interaction Analysis (BIA) of the interaction between selected variants and rVIII. The ligands were immobilized by amine coupling onto the carboxylated dextran layer of a CM5 sensor chip (research grade) (Biacore AB) according to the manufacturer's recommendations. All analyses were performed at +25° C., the flow rate was 5 µl/min and the injected sample volume was 35 µl, unless otherwise stated. The surfaces were regenerated with 10 µl 10 mM NaOH, 1 M NaCl.

Figure 2:
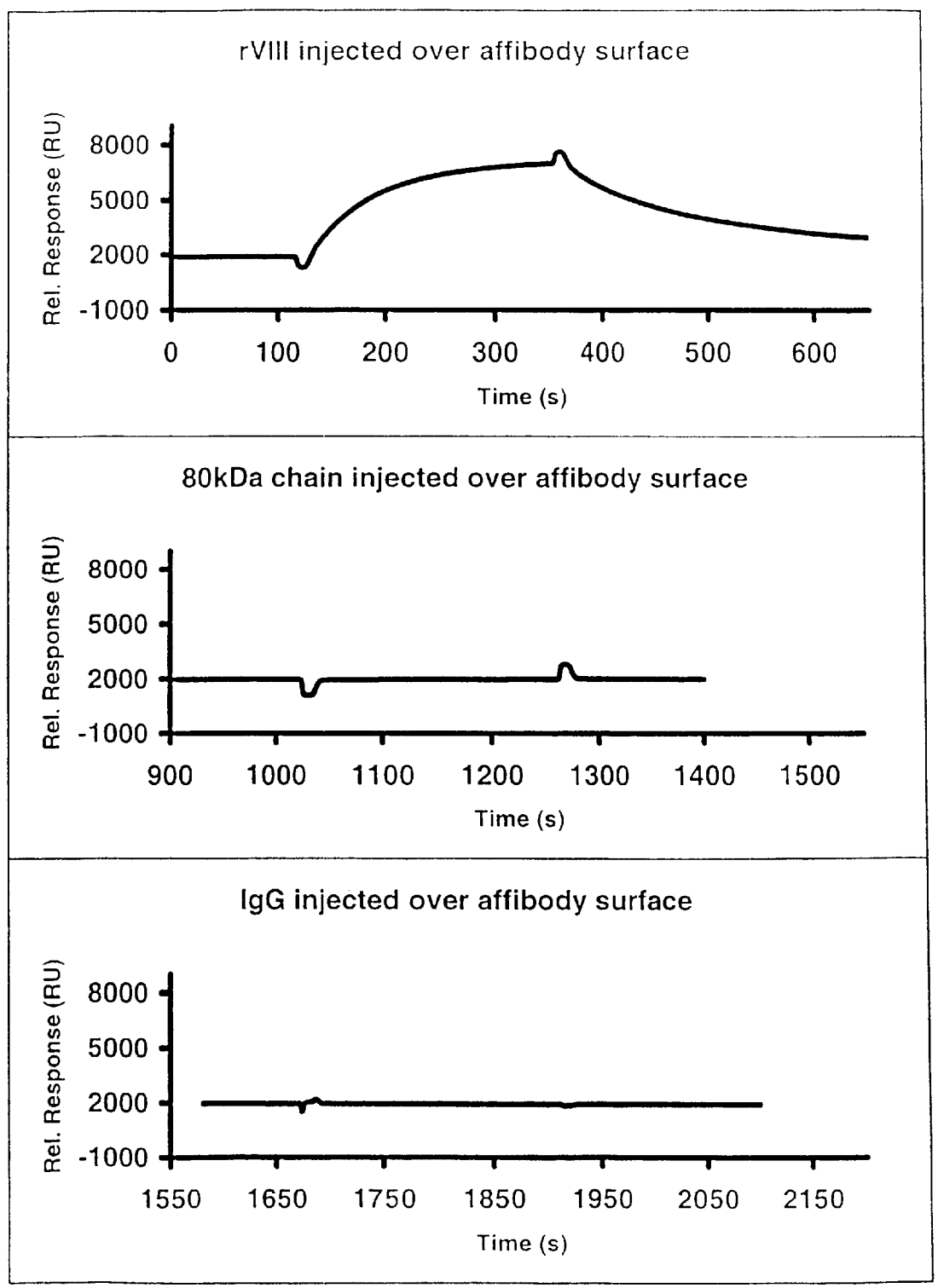

Injection of (i) rVIII, (ii) the 80 kDa chain of rVIII, or (iii) as a control polyclonal human IgG, over sensor chip surfaces coated with 1000 to 2500 resonance units (RU) of the selected affibody variants, demonstrated a significant response only for rVIII (80+90 kDa chain variant) for five of the affibodies ($Z_{fVIII:1}$ to $Z_{fVIII:5}$; SEQ ID NOS: 2 to 6), indicating that the binding is directed to the 90 kDa chain of rVIII and that the affinity towards IgG (Fc), displayed by the parental Z domain, is lost as expected. FIG. 2 shows the results obtained with affibody $Z_{fVIII:3}$ (SEQ ID NO: 4).

For one of the affibodies ($Z_{fVIII:6}$; SEQ ID NO: 7), a response was obtained both when injecting rVIII and the 80 kDa chain alone, indicating that the binding is directed to at least part of the 80 kDa chain of rVIII.

Four of the degenerated residues (W9, R10, W13 and V14) were conserved among all the 90 kDa chain binders and two of the residues showed a preference for either lysine or arginine (R/K17 and R/K27). There was also a preference for leucine in position 35.

For determination of kinetic parameters, the affibodies $Z_{fVIII:1}$ to $Z_{fVIII:4}$ (SEQ ID NOS: 2 to 5) were immobilized onto different surfaces as above. A control sensor chip surface was prepared by NHS/EDC-activation immediately followed by deactivation with ethanolamine. Recombinant Factor VIII was injected at 14 different concentrations (0.25 nM to 1.25 µM) in a volume of 100 µl in random order over the surfaces at a flow rate of 20 µl/min. After each injection, the surfaces were regenerated with 10 mM NaOH, 1 M NaCl. The rVIII responses were subtracted by the responses from the blank surface for each concentration and for each affibody surface. The dissociation and association rate constants were calculated using the BIA evaluation 2.1 software (BIAcore AB) according to the standard protocol for a one-to-one interaction model. The apparent overall dissociation constants ($K_D$) for the investigated variants were calculated to the range $1-2 \times 10^{-7}$ M.

Example 5

Competitive Binding Assay (First Generation Affibodies)

Figure 3:
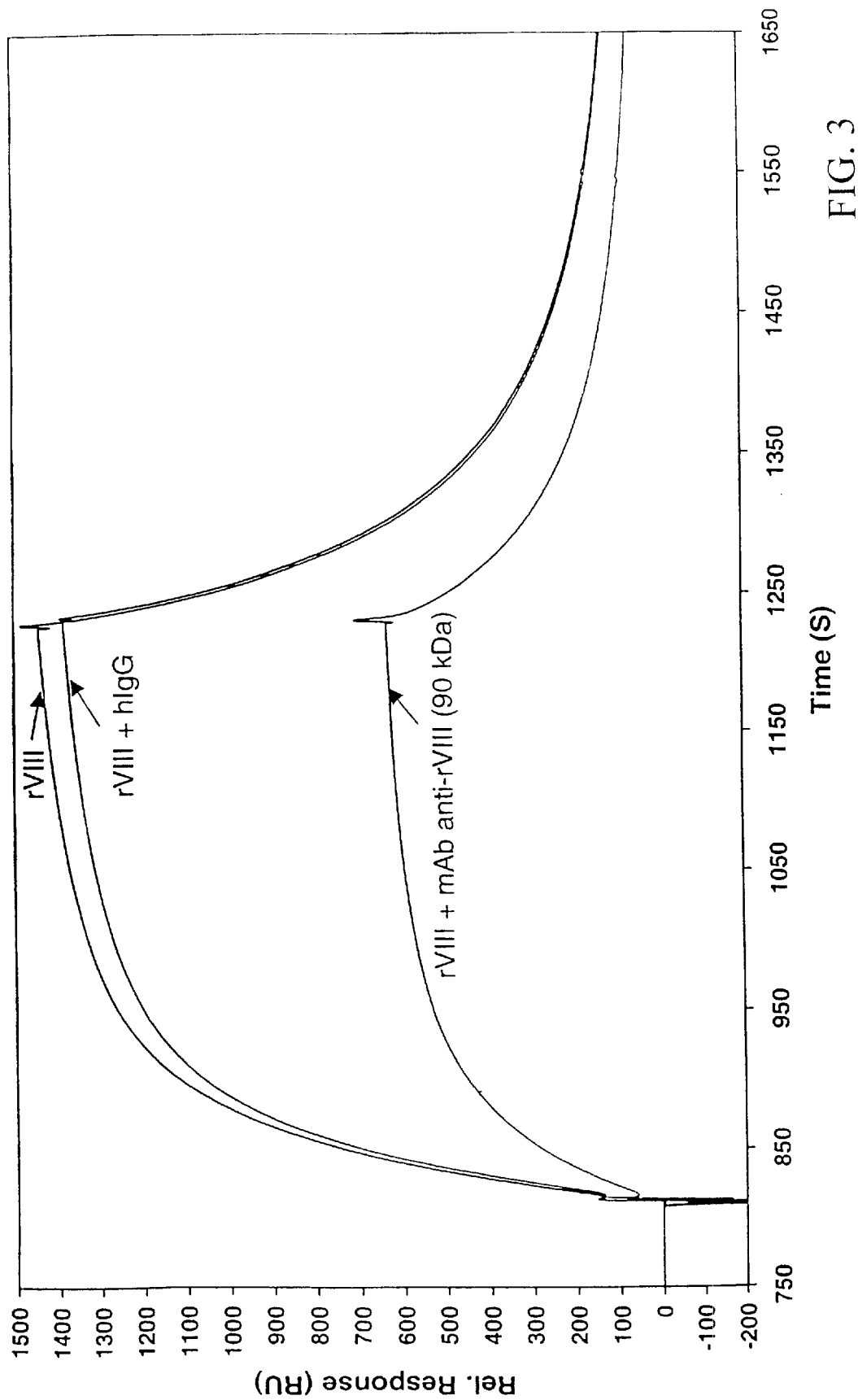

In order to further localize the binding site for the affibodies on the 90 kDa chain of rVIII, a monoclonal antibody designated 8A4, having a previously mapped binding interaction with the 90 kDa chain of rVIII, was used. BIA analysis was performed and three different injections were made over the affibody surfaces: (a) pure rVIII (42 nM); (b) rVIII (42 nM) mixed with 17 nM mAb 8A4; and (c) as a control, rVIII (42 nM) mixed with a 26-fold molar excess (1.1 µM) of polyclonal human IgG. The results, shown in FIG. 3, indicate a decrease in binding of rVIII to the affibody surfaces only when premixed with mAb 8A4, indicating that the affibody and mAb 8A4 compete for at least overlapping epitopes on rVIII.

Example 6

Affinity Chromatography of Factor VIII on an Affibody Column

The affibody designated $Z_{fVIII:3}$ was coupled to a HiTrap® affinity column packed with 1 ml NHS-activated Sepharose® High Performance (Amersham Pharmacia Biotech, Uppsala, Sweden) according to the manufacturer's recommendations, resulting in approximately 2 mg of coupled $Z_{fVIII:3}$-ABD fusion protein. The column was connected to an ÄKTA™ explorer 10 system (Amersham Pharmacia Biotech, Uppsala, Sweden) and equilibrated with 5 column volumes of binding buffer (0.1 M ammonium acetate, 5 mM calcium chloride, 0.8 M sodium chloride, 0,02 % Tween-20, pH 6.1) before loading of the sample. One ml of sample containing rVIII (0.1 mg/ml in binding buffer) was applied onto the column with a flow rate of 1 ml per minute. After washing with three column volumes of binding buffer and four column volumes of washing buffer (50 mM calcium chloride, 50 mM histidine, 0.05% Tween-20, pH 6.6), the captured protein was eluted with either 0.3 M acetic acid, pH 3.2 or elution buffer (50 mM calcium chloride, 50 mM histidine, 0.02% Tween-20, 50% ethyleneglycol, pH 6.6) and monitored by UV detection at 280 nm. SDS-PAGE analysis of the eluted fractions showed highly purified rVIII.

Example 7

Factor VIII Activity Assay

A Factor VIII activity assay was performed to determine the content of rVIII in the sample loaded on the affinity column, the flow through fractions and the eluted fractions. The activity assay was performed essentially as described by Rosen (1984) J. Haematol. Vol. 33, Suppl. 40, 139–145; and by Carlebjörk et al. (1987) Thrombosis Research Vol. 47, 5–14.

In this assay, Factor Xa (activated Factor X) is generated via the intrinsic pathway where Factor VIII:C is acting as a co-factor. Factor Xa is then determined by the use of a synthetic chromogenic substrate in the presence of a thrombin inhibitor to prevent hydrolysis of the substrate by thrombin. The reaction is terminated with acid and the Factor VIII:C activity, which is proportional to the release of paranitroaniline (pNA), is determined photometrically at 405 nm.

The flow through fractions did not show any Factor VIII activity, while the eluted fractions did, indicating that the affibody column was capable of binding rVIII, which subsequently could be eluted in functional form.

Example 8

Binding Studies Using Synthetic Affibody

A synthetic affibody (SEQ ID NO: 40), based on $Z_{fVIII:3}$ (SEQ ID NO: 4) and having an extra cystein residue at the C-terminal end, was produced by peptide synthesis according to known methods. The synthetic affibody enabling directed coupling, via the cystein residue, onto a BIA sensor chip surface. The synthetic affibody was thus immobilized by ligand thiol coupling onto the carboxylated dextran layer of a CM5 sensor chip (research grade) (Biacore AB) according to the manufacturer's recommendations and resulted in the immobilization of 450 RU. A control surface was prepared by activation followed by deactivation. The analyses were performed at +25° C., the flow rate was 5 μl/min, the injected sample volume was 25 μl and the regeneration was performed with 0.05% SDS. rVIII was injected over the surfaces and the rVIII response was subtracted by the response from the blank surface. A significant response was obtained (FIG. 4a), indicating that the affibody had been successfully synthesized and was correctly folded.

Plasma-derived Factor VIII (Octonativ-M, Pharmacia & Upjohn AB) was used in the binding study (Nilsson et al. pp. 193–206 In: Smith Sibinga et al. (eds.) Coagulation and Blood Transfusion (Proc. Fifteenth Ann. Symp. Blood Transfusion, Groningen 1990) Kluwer Academic Publishers, 1991). The plasma-derived Factor VIII was purified using immunoaffinity and ion-exchange chromatography essentially according to "Method M" (Griffith, M. (1991) Ann Hematol. 63, 131–137).

A sample containing purified plasma-derived Factor VIII was injected over the same surfaces under the same conditions as above (FIG. 4b). The difference in binding profile from rVIII can be due to the occurrence of different forms of Factor VIII in plasma, in addition to the association of Factor VIII with von Willebrand's factor.

A negative control experiment where the blood plasma was injected over wild-type Z (SEQ ID NO: 1) did not result in any response, indicating that the synthetic affibody bound specifically to factor VIII in the plasma.

Example 9

Construction of a Second Generation Library for Selection of rVIII-specific Affibodies With Improved Affinities A second generation combinatorial library of SPA domain Z sequences was prepared, as essentially described in Example 1, for selection of improved binding (affinity matured) polypeptides directed to recombinant Factor VIII. Five of the 13 residues in the second generation library were fixed; tryptophan, arginine, tryptophan, valine and arginine in residues 9, 10, 13, 14 and 27, respectively, while in residue number 17, the amino acid was fixed to either lysilne or arginine by an A(A/G)G degeneracy codon. The remaining 7, of the 13 surface located residues, were targeted for re-randomization using NN(G/T) degeneracy, as for the native library.

Example 10

Selection of Second Generation Affibodies

Biopanning against rVIII using the constructed second generation library, was performed with biotinylated rVIII immobilized on streptavidin coated paramagnetic beads, as described in Example 2. The rounds of biopanning were performed with an excess of the 80 kDa chain from Factor VIII, as in Example 2, in order to eliminate most of the potential 80 kDa binders. Increasing stringency throughout the panning cycles was achieved with an extended number of washing steps and a decreased amount of immobilized rVIII. All elution steps were performed with 50% ethylene glycol.

DNA sequencing of the phagemid inserts in 18 clones from panning cycle 4, 10 clones from cycle 5, and 8 clones from cycle 6, revealed that two pairs of clones were identical. The selected affibodies having unique sequences are shown in FIG. 1 and in the Sequence Listing as SEQ ID NOS: 8 to 22 (cycle 4); SEQ ID NOS: 23 to 31 (cycle 5) and SEQ ID NOS: 32 to 39 (cycle 6).

Some analogy with respect to amino acid type was detected in the 8 selected clones from panning cycle 6 (SEQ ID NOS: 32 to 39). Positions 24, 32 and 35 all contained a hydrophobic amino acid; there was a preference for aspartic or glutamic acid in position 28; and position 17 was conserved to lysine (see FIG. 1).

The selected affibodies from cycle 6 were produced from their phagemid constructs as described in Example 3.

Example 11

Binding Studies Using Second Generation Affibodies

Figure 5:
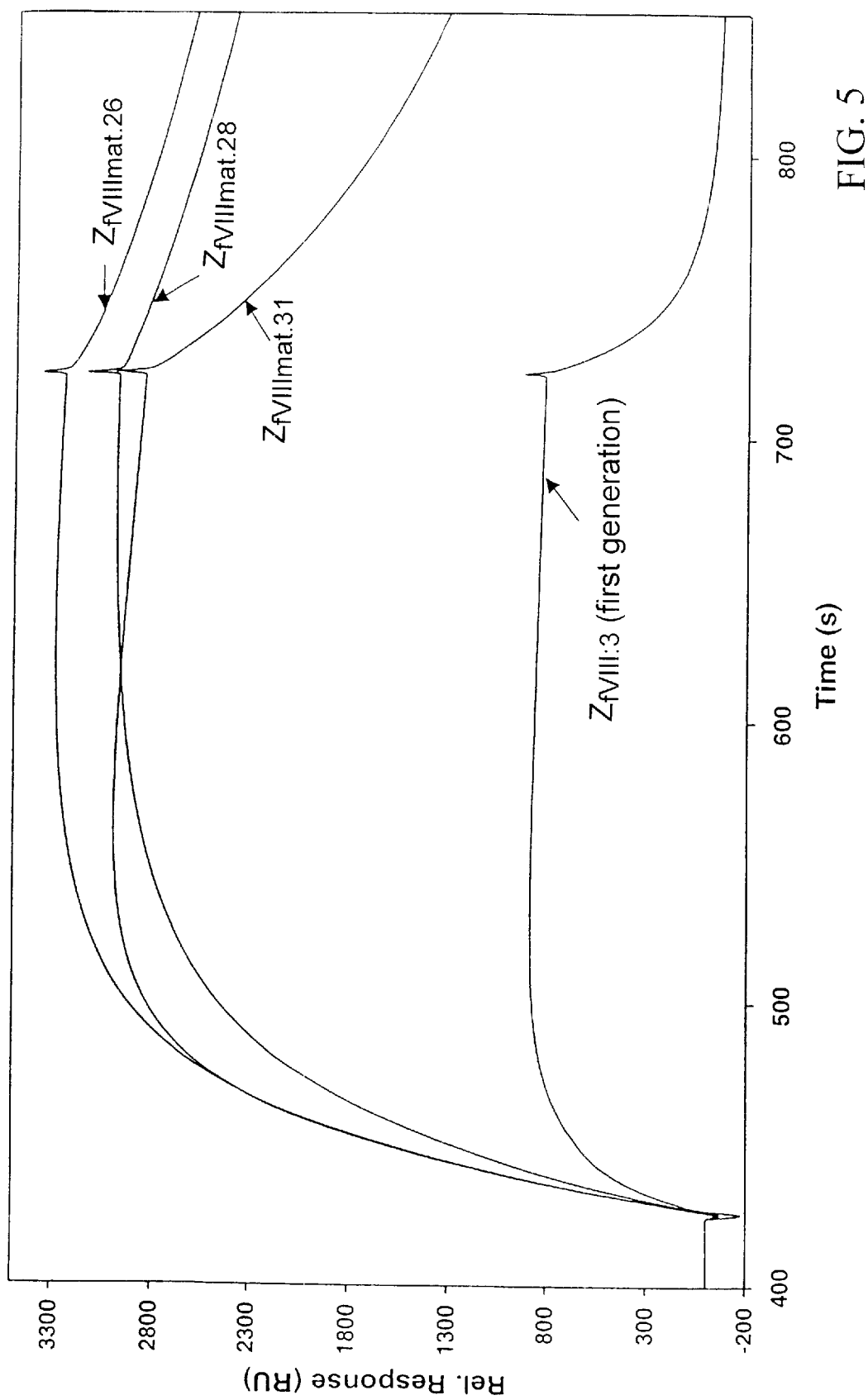

For ranking of the selected second generation affibodies, real time Biospecific Interaction Analysis (BIA) was used. A chip surface was immobilized with human serum albumin (HSA) and the affibodies were injected individually at a concentration of 1.4 μM over the HSA-surface, followed by injection of rVIII (30 nM). One of the first generation affibodies, $Z_{fVIII:3}$, was included in the ranking for comparison. All of the eight second generation affibodies showed a greater affinity towards rVIII compared to the $Z_{fVIII:3}$ affibody. FIG. 5 illustrates the results obtained with affibodies $Z_{fVIII\ mat.26}$, $Z_{fVIII\ mat.28}$ and $Z_{fVIII\ mat.31}$.

For calculation of kinetic parameters, rVIII was injected at 16 different concentrations over the surfaces with affibodies $Z_{fVIII\ mat.26}$, $Z_{fVIII\ mat.28}$ and $Z_{fVIII\ mat.31}$, respectively. The association and dissociation rates were determined, resulting in an apparent overall dissociation constant (KD) in the range of $5-10\times10^{-9}$ M for the three affibodies.

Two different monoclonal antibodies designated mAb 8A4 (having binding specificity for the 90 kDa chain of Factor VIII) and niAb 2B5 (having binding specificity for the 80 kDa chain of Factor VIII) were used for localization of the binding sites for the three affibodies mentioned above. BIA analysis was performed and four different injections over the surfaces were made; pure rVIII, rVIII mixed with mAb 8A4, rVIII mixed with mAb 2B5 and rVIII mixed with polyclonal human IgG. The results indicate an increase in binding of rVIII mixed with mAb 2B5 and a decrease in binding of rVIII mixed with mAb 8A4 to all three affibody surfaces. The increased signal seen with mAb 2B5 is explained by the presence on rVIII of separate epitopes for mAb 2B5 and the affibody, which means that rVIII binds simultaneously to these two entities which increases the mass of the bound complex. Furthermore, there was no obvious difference between the binding of pure rVIII compared to the binding of rVIII mixed with polyclonal human IgG to the affibody surfaces. Thus, the second generation affibodies bind to the 90 kDa chain of rVIII, as expected, and the mAb 8A4 and the affibodies compete for at least overlapping epitopes on rVIII.

SEQUENCE LISTING FREE TEXT

In the Sequence Listing placed at the end of this patent specification, the following "Free text" is included for SEQ ID NOS: 2 to 40 under numeric identifier <223> (Other information): "Description of Artificial Sequence: Modified bacterial receptor sequence"

What is claimed is:

1. A polypeptide comprising a derivative of the staphylococcal protein A (SPA) Z domain amino acid sequence of SEQ ID NO:1, wherein the derivative comprises between 4 and 20 substitutions of amino acid residues of the SPA Z domain, wherein at least the amino acid residues in positions 9, 10, 13 and 14 in SEQ ID NO:1 have been substituted by other amino acid residues, and wherein the derivative binds to at least one domain of a human Factor VIII protein.

2. The polypeptide according to claim 1, wherein at least the amino acid residues in positions 9, 10, 13, 14 and 17 in SEQ ID NO:1 have been substituted by other amino acid residues.

3. The polypeptide according to claim 1, wherein one or more of the amino acid residues in positions 11, 18, 24, 25, 27, 28, 32 or 35 in SEQ ID NO:1 have been substituted by other amino acid residues.

4. The polypeptide according to claim 1, wherein the domain of the human Factor VIII protein is the 90 kDa domain.

5. The polypeptide according to claim 1, wherein in SEQ ID NO:1, the amino acid residue in position 9 has been substituted by a tryptophan (W) residue, the amino acid residue in position 10 has been substituted by an arginine (R) residue, the amino acid residue in position 13 has been substituted by a tryptophan (W) residue, and the amino acid residue in position 14 has been substituted by a valine (V) residue.

6. The polypeptide according to claim 1, wherein the amino acid residue in position 17 in SEQ ID NO:1 has been substituted by an arginine (R), lysine (K), glycine (G), or alanine (A) residue.

7. The polypeptide according to claim 1, wherein the amino acid residue in position 35 in SEQ ID NO:1 has been substituted by a glycine (G), tryptophan (W), leucine (L), arginine (R), tyrosine (Y), valine (V), or phenylalanine (F) residue.

8. The polypeptide according to claim 6, wherein the amino acid residue in position 17 in SEQ ID NO:1 has been substituted by a lysine (K) residue.

9. The polypeptide according to claim 7, wherein the amino acid residue in position 35 in SEQ ID NO:1 has been substituted by a leucine (L) residue.

10. The polypeptide according to claim 1, wherein the polypeptide comprises an amino acid sequence set forth in any one of SEQ ID NOS:2 to 6, or 8 to 40.

11. The polypeptide according to claim 1, wherein the domain of human Factor VIII protein is the 80 kDa domain.

12. The polypeptide according to claim 11, wherein the polypeptide comprises the amino acid sequence set forth in SEQ ID NO:7.

13. The polypeptide according to claim 1, wherein the amino acid residue in position 24 in SEQ ID NO:1 has been substituted by a tryptophan (W), tyrosine (Y), or phenylalanine (F) residue.

14. The polypeptide according to claim 13, wherein the amino acid residue in position 24 in SEQ ID NO:1 has been substituted by a tryptophan (W) residue.

15. The polypeptide according to claim 1, wherein the derivative preferentially binds the human Factor VIII protein in a competitive binding assay with IgG.

16. The polypeptide according to claim 1, wherein the derivative does not bind to IgG.

* * * * *